United States Patent [19]

Arnold et al.

[11] Patent Number: 4,892,953

[45] Date of Patent: Jan. 9, 1990

[54] BENZTHIAZOLE SUBSTITUTED DIACID TERPHENYL MONOMERS

[75] Inventors: Fred E. Arnold, Centerville; Jerry L. Burkett, Troy, both of Ohio

[73] Assignee: The United States of America as represented by the Secretary of the Air Force, Washington, D.C.

[21] Appl. No.: 227,978

[22] Filed: Jul. 29, 1988

[51] Int. Cl.$^4$ .............................. C07D 277/66
[52] U.S. Cl. .................... 548/156; 528/176; 528/337
[58] Field of Search ........................ 548/156

[56] References Cited

U.S. PATENT DOCUMENTS

| | | | |
|---|---|---|---|
| 4,108,835 | 8/1978 | Arnold et al. | 528/183 |
| 4,131,748 | 12/1978 | Arnold et al. | 562/488 |
| 4,533,692 | 8/1985 | Wolfe et al. | 524/417 |
| 4,533,693 | 8/1985 | Wolfe et al. | 524/417 |

*Primary Examiner*—Robert Gerstl
*Attorney, Agent, or Firm*—Charles E. Bricker; Donald J. Singer

[57] ABSTRACT

Phenylbenzthiazole-substituted p-terphenylene dicarboxylic acids of the formula

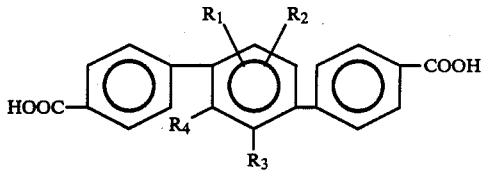

wherein $R_1$ is —H or

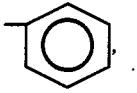

$R_2$ is

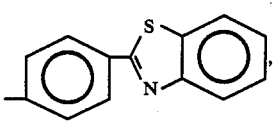

$R_3$ is

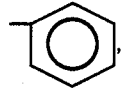

and $R_4$ is $R_2$ or

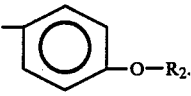

6 Claims, No Drawings

BENZTHIAZOLE SUBSTITUTED DIACID TERPHENYL MONOMERS

RIGHTS OF THE GOVERNMENT

The invention described herein may be manufactured and used by or for the Government of the United States for all governmental purposes without the payment of any royalty.

BACKGROUND OF THE INVENTION

This invention relates to p-terphenylene-dicarboxylic acid compounds having pendant heterocyclic groups.

In general, the class of aromatic heterocyclic extended chain polymers are well known for their outstanding thermal, physical and chemical properties. These polymers generally exhibit excellent modulus and tenacity properties, but lack good properties when in compression, which limits their use as reinforcing structural fibers.

It is an object of the present invention to provide novel benzthiazole-substituted dicarboxylic acid p-terphenyl monomers. These monomers may be used for making aromatic heterocyclic polymers which exhibit improved compressive properties.

Other objects, aspects and advantages of the present invention will be apparent to those skilled in the art from a reading of the following detailed disclosure of the invention.

SUMMARY OF THE INVENTION

In accordance with the present invention there are provided phenylbenzthiazole-substituted p-terphenylene dicarboxylic acids of the formula

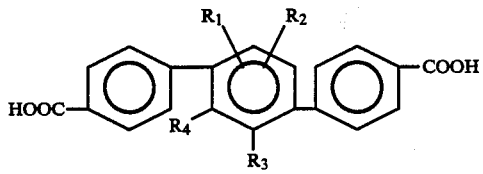

wherein $R_1$ is —H or

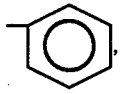

$R_2$ is

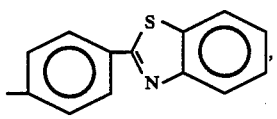

$R_3$ is

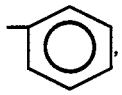

and $R_4$ is $R_2$ or

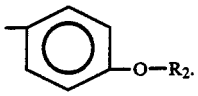

DESCRIPTION OF THE PREFERRED EMBODIMENTS

The phenylbenzthiazole-substituted p-terphenylene dicarboxylic acids (I) are prepared as illustrated by the following equations:

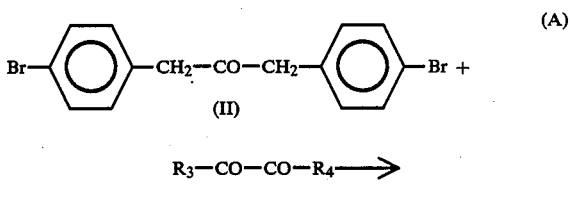

(A)

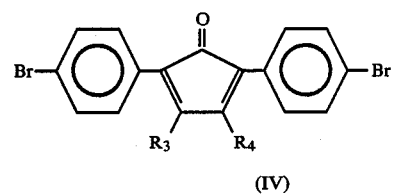

(B)

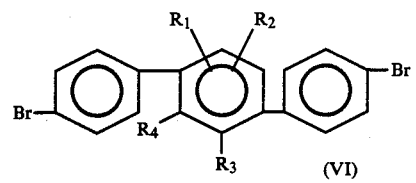

(C)

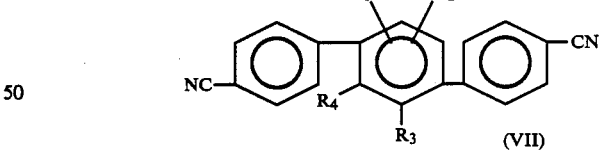

(D)

As shown by equation (A), a benzthiazole-substituted benzil (III) is reacted with 1,3-bis(p-bromophenyl)-2-propanone (II) to form a cyclopentadieneone (IV). Substantially equimolar amounts of compounds (II) and (III) are utilized. The reaction is carried out in the presence of an alkali metal hydroxide or an organoammonium hydroxide under reflux conditions in a suitable reaction medium. An alcohol, such as ethanol, propanol, butanol, or the like, can be conveniently used as the reaction medium. The amount of the hydroxide can vary within rather broad limits but generally ranges from about 0.1 to 0.75 mole per mole of the benzil. The reaction mixture is usually maintained under reflux condition for a period of about 15 minutes to 8 hours.

In the second part of the synthesis as shown by equation (B), compound (IV) prepared above is reacted with an acetylenic compound (V) to form the dibromo terphenyl compound (VI). In conducting the reaction a molar excess of the acetylenic compound is used, e.g. 1.5 to 10 moles per mole of compound (IV). The reaction is carried out in a suitable reaction medium, such as a chlorinated hydrocarbon, under reflux conditions for a period of about 15 minutes to 24 hours.

In the third part of the synthesis, compound (VI) is reacted with cuprous cyanide to form the corresponding dicyano terphenyl compound (VII). A molar excess of cuprous cyanide, e.g., 1.5 to 15 moles per mole of compound (VI) is used. The reaction is carried out in an inert atmosphere under reflux conditions, utilizing a suitable reaction medium, such as N-methyl-2-pyrrolidone. A reaction period of about 8 to 24 hours is usually sufficient to affect the substitution of the bromine atoms with cyano groups.

In the fourth and final part of the synthesis, the dicyano terphenyl compound (VII) is hydrolyzed to provide the p-terphenylene dicarboxylic acids (I) of this invention. The reaction may be carried out in phosphoric acid at an elevated temperature of about 160° to 180° C. for about 1 to 8 hours.

The benzil compounds (III) are prepared as follows:

4-(2-benzthiazole) benzil may be prepared by the oxidation of 2-(4-phenylethynylphenyl) benzthiazole using an oxidizing agent such as potassium permanganate. The reaction is carried out in a suitable reaction medium, such as methylene chloride, under reflux conditions for about 4 to 24 hours.

4-(4-oxyphenyl benzthiazole) benzil may be prepared by reacting 2-(4-hydroxy phenyl) benzthiazole with 4-nitrobenzil under anhydrous conditions in a suitable solvent, such as dimethylsulfoxide, in the presence of a weak base, such as potassum carbonate at a temperature of about 80° to 100° C. for about 4 to 24 hours.

The acetylenic benzthiazoles are prepared as follows:

2-(4-phenylethynyl phenyl) benzthiazole may be prepared by reacting phenylacetylene with 2-(4-bromophenyl) benzthiazole in a suitable solvent in the presence of a suitable catalyst. A suitable preparation is described by Reinhardt et al, U.S. Pat. No. 4,547,592, the portion of which describing reaction conditions and the catalyst system is incorporated herein by reference.

2-(4-Ethynylphenyl) benzthiazole may be prepared by the method described by Tsai et al, U.S. Pat. No. 4,559,404, which is incorporated herein by reference.

The phenylbenzthiazole-substituted p-terphenylene dicarboxylic acids of this invention are useful in preparing polymers having repeating units of the formula

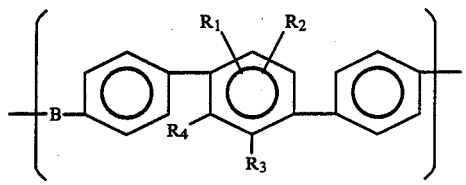

wherein $R_1$, $R_2$, $R_3$ and $R_4$ are as described previously and B is

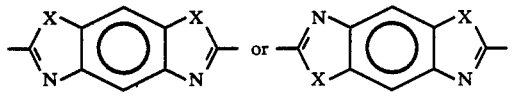

wherein X is —S—, —O— or —NH—; and copolymers having repeating units of the formula

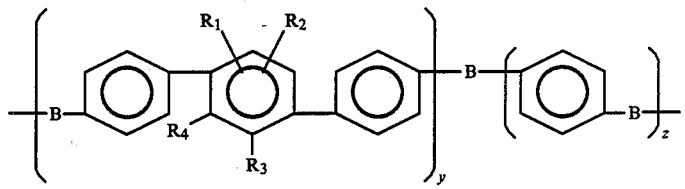

wherein $R_1$, $R_2$, $R_3$, $R_4$ and B are as described previously, y ranges from about 0.02 to 0.20 and z is 1.0-y. These polymers and copolymers may be formed into fibers of high quality. Preparation of the polymers and copolymers are described in our co-pending applications Ser. Nos. 07/227,977 and 07/227,979, filed of even data herewith.

The following examples illustrate the invention:

EXAMPLE I 4-(4-Phenyl-2-benzthiazole)-2-methyl-3-butyn-2-ol.

To a solution containing 2-(4-bromophenyl)benzthiazole (23 g, 0.079 mol) and 2-methyl-3-butyn-2-ol (30.3 g, 0.36 mol) in 250 ml of triethylamine was added the catalyst system, consisting of dichlorobis-(triphgenylphosphine)palladiumII (0.5 g), triphenyl-phosphine (0.15 g), and cuprous iodide (0.05 g). The reaction mixture was refluxed under a nitrogen atmosphere for 22 h. After cooling to 25° C., the reaction mixture was filtered and the triethylamine was removed under reduced pressure to give 50 g of crude product. The material was dissolved in methylene chloride and filtered through silica gel. Removal of the methylene chloride under reduced pressure and recrystallization of the resulting solid from toluene afforded 18 g (77.4%): m.p. 170°–172° C.

analysis Calcd. for $C_{18}H_{15}NOS$: C, 73.69; H, 5.15; N, 4.77. Found: C, 73.66; H, 5.22; N, 4.68.

2-(4-Ethynylphenyl)benzthiazole.

A solution of 4-(4-phenyl-2-benzthiazole-2-methyl-3-butyn-2-ol (14.8 g, 0.05 mol) in 600 ml of benzene was formed with heating under nitrogen in a three necked, 1 L. round-bottom flask which was equipped with a Dean-Stark trap, condenser, magnetic stir bar, and a gas inlet/outlet adapter. A (5%) methanolic potassium hydroxide solution (20 ml) was added and the mixture stirred and heated at reflux for 2.5 h. Acetone formed as the reaction progressed and was removed by azeotropic distillation with benzene. The benzene was filtered through a bed of silica gel and removed under reduced pressure. The resulting yellow solid was recrystallized from heptane to give 7.8 g (82.5%) of light yellow crystals: m.p. 129°–130° C.

Analysis Calcd. for $C_{15}H_9NS$: C, 76.56; H, 3.85; N, k5.95. Found: C, 76.58; H, 3.81; n, 5.96.

EXAMPLE II 2-(4-Phenylethynylphenyl)benzthiazole.

To a solution containing 2-(4-bromophenyl)benzthiazole (43.5 g 0.15 mol) and phenylacetylene (20 g, 0.19 mol) in 0.8 L of triethylamine was added the catalyst system consisting of dichlorobis-(triphenylphosphine)palladiumII (1 g), triphenylphosphine (0.3 g) and cuprous iodide (0.1 g). The reaction mixture was refluxed under a nitrogen atmosphere for 19 h. After cooling to 25° C., the reaction mixture was filtered and the filtrate poured into 3 L of water. The resulting light gray solid was isolated by filtration and dried in an oven at 110° C. Recrystallization from heptane using activated charcoal gave 37 g (78.9%) of a white crystalline product: m.p. 172°–173° C.

Analysis Calcd. for $C_{21}H_{14}NS$: C, 80.73; H, 4.52; N, 4.48. Found: C, 80.91; H, 4.37; N, 4.31.

EXAMPLE III 4-(4-Oxyphenylbenzthiazole)benzil.

To a solution containing 2-(4-hydroxyphenyl)benzthiazole (15.8 g, 0.069 mol) and 4-nitrobenzil (21.5 g, 0.08 mol) in 250 ml of anhydrous DMSO was added potassium carbonate (28 g, 0.20 mol). The reaction mixture was stirred at room temperature for 0.5 h, and then heated to 90° C. and maintained at that temperature for 16 h. On cooling to room temperature, the product was isolated by precipitation into water and extracting the aqueous suspension with methylene chloride. Filtration of the methylene chloride extract through magnesium sulfate and removal of the solvent under reduced pressure led to 28 g of crude benzil. Recrystallization from isopropanol using activated charcoal gave 22.2 g (92%) of product: m.p. 150°–151° C.

Analysis Calcd. for $C_{27}H_{17}NOS$: C, 74.46; H, 3.94; N, 3.22. Found: C, 74.14; H, 4.01; N, 3.12.

EXAMPLE IV 4-benzthiazole benzil.

to a solution of 2-(4-phenyl ethynylphenyl)benzthiazole (34 g, 0.10 mol) in 800 ml of methylene chloride was added potassium permanganate (20 g, 0.126 mol) in 500 ml of water and 4.0 g (Adogen 464) in 50 ml of glacial acetic acid. The reaction mixture was refluxed for 5 h and an additional (10 g, 0.063 mol) of potassium permanganate was added and refluxed another 18 h. On cooling at room temperature, the reaction mixture was transferred to a 3 L beaker and stirred with sodium bisulfite until clear. The methylene chloride layer was separated, washed several times with water, and filtered though magnesium fulfate. The methylene chloride was removed under reduced pressure to give a yellow solid which was air-dried. The product was recrystallized from isopropanol using activated charcoal to give 26.3 g (90.8%): m.p. 182°–184° C.

Analysis Calcd. for $C_{21}H_{13}NO_2S$: C, 73.44; H, 3.81; N, 4.10. Found: c, 73.53; H, 4.05; N, 4.18.

EXAMPLE V 2.5-Bis(p-bromophenyl)-3-phenyl-4-(2-[4-phenoxyphenyl]-benzthiazole)cyclopenetadienone.

A mixture of 4-(4-oxyphenylbenzthiazole)benzil (13.06 g, 0.03 mol) and 1,3-bis(p-bromophenyl)-2-propanone (11.04 g, 0.03 mol) in 1.2 liters of n-butanol was heated under a nitrogen atmosphere to 60° C. To the resulting homogeneous solution was added 1.2 g of potassium hydroxide dissolved in 100 ml of methanol. The mixture was heated to 60° C. for 3 h. After cooling to 0° C., the purple crystalline product was isolated by filtration, washed with methanol, and air-dried to give 11.4 g (49.6%): m.p. 203°–205° C.

Analysis Calcd. for $C_{42}H_{25}NOSBr_2$: C, 65.72; H, 3.28; N, 1.82. Found: C, 65.55; H, 3.47; N, 1.83.

EXAMPLE VI 2,5-Bis(p-bromophenyl)-3-phenyl-4-(2-phenylbenzthiazole)cyclopentadienone.

A mixture of 4-(2-phenylbenzthiazole)benzil (9.3 g, k0.027 mol) and 1,3-bis(p-bromophenyl)-2-propanone (11.2 g, 0.03 mol) in 1.5 liters of proganol was heated to 85° C. to form a homogeneous solution. To the solution at 80° C. was added 4 ml of a 40% methanolic benzyltrimethyl ammonium hydroxide solution. On addition of the base a bright purple color developed which on further heating for 2.5 h formed a purple solid. After cooling to 15° C., the product was isolated by filtration, washed with methanol, then heptane, and dried at 120° C. to give 13.5 g (74%): m.p. 273°–275° C.

Analysis Calcd. for $C_{36}H_{21}NOSBr_2$: C, 64.02; H, 3.13; N, 2007. Found: C, 63.98; H, 3.32; N, 2.03.

EXAMPLE VII 4,4''-Dibromo-2',5'-diphenyl-3',6'-[2-(4-phenylbenzthiazole)]-p-terphenyl.

A mixture of 2-(4-phenylethynylphenyl)-benzthiazole (13.1 g, 0.042 mol), 2,5-bis(p-bromophenyl)-3-phenyl-4-(2-phenylbenzthiazole)cyclopentadienone (26.8 g, 0.032 mol) and 200 ml of 1,2,4-trichlorobenzene was refluxed under a nitrogen atmosphere for 16 h. After cooling to 25° C., the solution was precipitated by pouring into 3 L of petroleum ether to give a light yellow solid which was collected by filtration and dried at 110° C. The product was recrystallized from xylene to give 13.5 g (35.5%) of light yellow crystals: m.p. >360° C.

Analysis Calcd. for $C_{56}H_{34}N_2S_2Br_2$: C, 70.15; H, 3.57; N, 2.92. Found: C, 70.16; H, 3.75; N, 3.48.

EXAMPLE VIII 4,4''-Dicyano-2',5'-diphenyl-3',6'-[2-(4-phenylbenzthiazole)]-p-terphenyl.

A mixture of 4,4''-dibromo-2,5'-diphenyl-3',6'-[2-(4-phenylbenzthiazole)]-p-terphenyl (28.8 g, 0.03 mol), cuprous cyanide (28.5 g, 0.31 mol), and dry N-methyl-2-pyrrolidone (300 ml) was added under a nitrogen atmosphere. After heating under reflux for 21 h, the cooled reaction mixture was poured into 1.5 L of water containing 116 g of sodium cyanide. The resulting gray precipitate was washed with 10 percent aqueous sodium cyanide and dried in an oven at 100° C. The crude product was dissolved in methylene chloride, passed though a silica gel column, and eluted with methylene chloride. Removal of the solvent under reduced pressure gave 16.5 g (64.6%) of white crystals: m.p. >360° C.

Analysis Calcd. for $C_{58}H_{34}N_4S_2$: C, 81.85; H, 4.27; N, 6.58. Found: C, 81.83; H, 4.21; N, 6.53.

EXAMPLE IX 4,4''-Dicarboxy-2',5'-diphenyl-3',6'-[2-(4-phenylbenzthiazole)]-p-terphenyl.

A solution of 4,4''-:dicyano-2',5'-diphenyl-3',6'-[2-(4-phenylbenzthiazole)]-p-terphenyl (11.6 g, 0.013 mol) and 540 g of phosphoric acid was heated under a nitrogen atmosphere to 177° C. and maintained at that temperature for 4 h. After cooling the solution to 25° C., it was poured into 3.5 L of water to precipitate a white solid. The solid was collected by filtration, washed with water, and air-dried. The diacid was purified by recrystallization from ethyleneglycol monoethylether using activated charcoal to give 9 g (74.4%): m.p. >360° C.

Analysis Calcd. for $C_{58}H_{36}N_2S_2O_4$: C, 78.35; H, 4.08; N, 3.15. Found: C, 78.21; H, 4.05; N, 3.51.

EXAMPLE X 4,4''-Dibromo-2'-phenyl-3',6'-[2-(4-phenoxyphenyl)-benzthiazole]-p-terphenyl.

A mixture of 2,5-bis(p-bromophenyl)-3-phenyl-4-(4-phenoxyphenyl)benzthiazole]cyclopentadienone (10.75 g, 0.014 mol), 2-(4-ethynylphenyl)benzthiazole (3.6 g, 0.015 mol), and 60 ml of o-dichlorobenzene was refluxed under a nitrogen atmosphere for 3 h. After cooling to 25° C., the solution was precipipated by pouring into 3 L of methanol. The product was collected by filtration, washed with methanol, and air-dried to give 12 g (87.9%): m.p. 175°–185° C.

Analysis Calcd. for $C_{56}H_{34}N_2OS_2Br_2$: C, 68.99; H, 3.52; N, 2.88. Found: C, 58.30; H, 3.64; N, 3.03.

EXAMPLE XI 4,4''-Dicyano-2'-phenyl-3',6'-[2-(4-phenoxyphenyl)-benzthiazole]-p-terphenyl.

A mixture of 4,4''-dibromo-2'-phenyl-3',6'-[2-(4-phenoxyphenyl)benzthiazole)-p-terphenyl (10.2 g, 0.01 mol), cuprous cyanide (4.15 g, 0.046 mol), and dry N-methyl-2-pyrrolidone (75 ml) was added under a nitrogen atmosphere. After heating under reflux for 17 h, the cooled reaction mixture was poured into 200 ml of water containing 30 g of sodium cyanide. The resulting gray precipitate was collected by filtration, washed with 10% aqueous sodium cyanide, and dried in an oven at 110° C. The crude product was dissolved in methylene chloride and passed though a silica gel column, eluting with methylene chloride. Removal of the solvent under reduced pressure gave 5.5 g (61%) of white crystals: m.p. 175°–185° C.

Analysis Calcd. for $C_{58}H_{34}N_4S_2O$: C, 80.34; H, 3.95; N, 6.46. Found: C, 79.64; H, 4.14; N, 6.19.

EXAMPLE XII 4,4''-Dicarboxy-2'-phenyl-3',6'-[2-(4-phenoxyphenyl)benzthiazole]-p-terphenyl.

a solution of 4,4''-dicyano-2'-phenyl-3',6'-[2-(4-phenoxyphenyl)benzthiazole]-p-terphenyl (14 g, 0.016 mol) and 350 g of phosphoric acid was heated under a nitrogen atmosphere to 170° C. and maintained at that temperature for 5.5 h. After cooling the solution to 25° C., it was poured into 3 L of water to precipitate a white solid. The solid was collected by filtration, washed with water, and dried in an oven at 120° C. The diacid was purified by recrystallization from a mixture of tetrahydrofuran/heptane using activated charcoal to give 14.5 g (99%): m.p. 255°–260° C.

Analysis Calcd. for $C_{58}H_{36}N_2S_2O_5$: C, 76.97; H, 4.01; N, 3.10. Found: C, 77.26; H, 4.20; N, 3.35.

EXAMPLE XIII 4,4''-Dibromo-2'-phenyl-3',6'-[2-(4-phenylbenzthiazole)]-p-terphenyl.

A mixture of 2-(4-Ethynylphenyl)benzthiazole (10.88 g, 0.0461 mol), 2.5 Bis(p-bromophenyl-3-phenyl-4-(2-phenylbenzthiazole) cyclopentadienone (31.44 g, 0.0465 mol) and 150 ml of 1,2 -dichlorobenzene was refluxed under a nitrogen atmosphere for 21 hours. After cooling to 25° C., the solution was precipitated by pouring into three liters of hexane to give light yellow crystals which were collected by filtration and dried 100° C. to give 42.1 g crude product. The crude product 42.1 g was dissolved in refluxing three liters methylene chloride, activated charcoal was added and solution was filtered. The solution was refluxed and 900 ml heptane was added. The solution was reduced to 900 ml in which the product started coming out of the solution. The solution was allowed to cool and yellow white crystals recrystallized. The yellow white crystals 36.3 g (89.2%) were recovered by filtration: m.p. 288° C. (shrinkage 203°–205° C.)

Analysis Calcd. for $C_{50}H_{30}N_2S_2Br_2$: C, 68.03; H, 3.43; N, 3.17. Found: C, 68.04; H, 3.44; N, 3.07.

EXAMPLE XIV 4,4''-Dicyano-2'-phenyl-3',6'-[2-(4-phenylbenzthiazole)]-p-terphenyl.

A mixture of 4,4''-dibromo 2'-phenyl-3',6'-[2-(4-phenylbenzthiazole)]-p-terphenyl (36.0 g, 0.0408 mol), cuprous cyanide (36.0 g, 0.40 mol), and dry N-methyl-2-pyrrolidone (200 ml) was under a nitrogen atmosphere. After heating under reflux for 17 hours, the cooled reaction mixture was poured into two liters of water containing 200 g of sodium cyanide. The resulting gray precipitate was washed with 10 percent aqueous sodium cyanide and washed repeatedly with water. The crude product was dried at 110° for 24 hours and weighed 31.9 g. The crude product was dissolved in methane chloride and passed through a silica gel column (two inch by 12 inch). The product was eluted off the column with 1.2 liters of methylene chloride. Removal of the solvent under reduced pressure gave 20.1 g (65.6%) of white crystals: m.p. 318°–329° C. (some shrinkage 290° C.)

Analysis Calcd. for $C_{50}H_{30}N_4S_2$: C, 79.97; H, 4.03; N, 7.46. Found: C, 80.17; H, 3.95; N, 6.96.

EXAMPLE XV 4,4''-Dicarboxy-2'-phenyl-3',6'-[2-(4-phenylbenzthiazole)]-p-terphenyl.

A solution of 4,4''-dicyano-2-phenyl-3',6'-[2-(4-phenylbenzthiazole)]-p-terphenyl (20.0 g, 0.0266 mol) and 800 g of phosphoric acid (100%) was heated under a nitrogen atmosphere to 175° C. and maintained at that temperature for four hours. After cooling the solution to 25° C., it was poured into 6.5 liters of water to precipitate a white solid. The solid was collected by filtration, washed with water repeatedly and dried in oven at 100° for 24 hours. The diacid was purified by dissolving in two liters refluxing tetrahydrofuran and using activated charcoal, the solution was filtered. The filtrate was refluxed with 1,000 ml heptane and the volume reduced to 800 ml. The solution was cooled and 20.0 g (94.4%) recrystalized a white crystal. m.p. 347°–357°.

Analysis Calcd. for $C_{52}H_{32}N_2S_2O_4$: C, 76.82; H, 3.97; N, 3.45. Found: C, 76.43; H, 4.03; N, 3.68.

Various modifications of the present invention can be made in view of the foregoing disclosure without departing from the spirit and scope of the invention.

We claim:

1. A phenylbenzthiazole-substituted p-terphenylene dicarboxylic acid of the formula

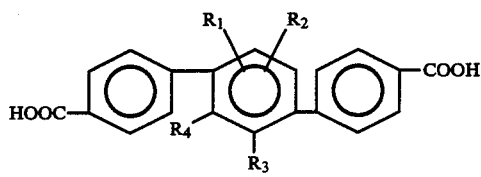

wherein $R_1$ is —H or

$R_2$ is

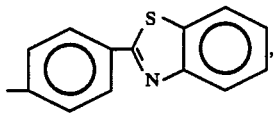

$R_3$ is

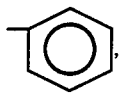

and $R_4$ is $R_2$ or

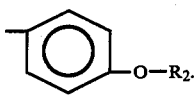

2. The dicarboxylic acid of claim 1, wherein $R_1$ is —H and $R_4$ is $R_2$.

3. The dicarboxylic acid of claim 1, wherein $R_1$ is —H and $R_4$ is

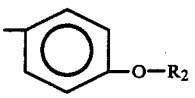

4. The dicarboxylic acid of claim 1, wherein $R_1$ is -phenyl and $R_4$ is $R_2$.

5. The dicarboxylic acid of claim 1, wherein $R_1$ is -phenyl and $R_4$ is

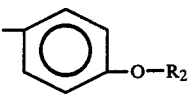

6. The compound 4,4''-dicarboxy-2'-phenyl-3',6'-[2-(4-phenoxyphenyl)benzthiazole]-p-terphenyl.

* * * * *

UNITED STATES PATENT AND TRADEMARK OFFICE
CERTIFICATE OF CORRECTION

PATENT NO.  : 4,892,953

DATED       : January 9, 1990

INVENTOR(S) : Fred E. Arnold et al

It is certified that error appears in the above-identified patent and that said Letters Patent is hereby corrected as shown below:

Col 7, lines 23-24, "2,5-bis(p-bromophenyl)-3-phenyl-4-(4-phenoxyphenyl)benzthiazole]cyclopentadienone" should read "2,5-bis(p-bromophenyl)-3-phenyl-4-[2-(4-phenoxylphenyl)-benzthiazole]cyclopentadienone".

Signed and Sealed this

Sixteenth Day of July, 1991

Attest:

HARRY F. MANBECK, JR.

*Attesting Officer*  *Commissioner of Patents and Trademarks*